United States Patent [19]

Popov et al.

[11] 4,317,883

[45] Mar. 2, 1982

[54] METHOD FOR OBTAINING OF GLUCOSE ISOMERASE

[75] Inventors: Mitko S. Popov; Galina M. Djedjeva; Ivan O. Todorov; Nelly S. Stoeva, all of Sofia, Bulgaria

[73] Assignee: Institute Po Microbiologia, Sofia, Bulgaria

[21] Appl. No.: 212,627

[22] Filed: Dec. 3, 1980

[51] Int. Cl.³ .............................................. C12N 9/92
[52] U.S. Cl. ..................................... 435/234; 435/886
[58] Field of Search .......................................... 435/234

[56] References Cited

U.S. PATENT DOCUMENTS

| | | | |
|---|---|---|---|
| 3,826,714 | 7/1974 | Suekane et al. | 435/234 X |
| 3,956,066 | 5/1976 | Coker et al. | 435/234 X |
| 3,979,261 | 9/1976 | Outtrup | 435/234 |
| 4,061,539 | 12/1977 | Lee | 435/234 X |
| 4,255,521 | 3/1981 | Hirohara et al. | 435/234 |
| 4,283,496 | 8/1981 | Lee | 435/253 |

*Primary Examiner*—Lionel M. Shapiro
*Attorney, Agent, or Firm*—Karl F. Ross

[57] ABSTRACT

A method for producing glucose isomerase comprising the steps of cultivating the enzyme producing strain Streptomyces sp. 1339 registration N. 144 Bulgarian State Institute for Drug Control, for 36 to 72 hours in a culture medium with xylose as an indicator, the temperature being kept at 24° to 36° C., the initial pH of cultivation being from 6.5 to 9.0 and effective isomerization at a temperature of 50° to 80° C., and a pH of 6.0 to 9.0 in the presence of $1 \times 10^{-4}$M $CoCl_2.6H_2O$ $1 \times 10^{-2}$M $MgSO_4.7H_2O$ in 0.1 to 3 M of the substrate.

2 Claims, No Drawings

METHOD FOR OBTAINING OF GLUCOSE ISOMERASE

The invention relates to a method for obtaining of glucose isomerase from a streptomyces strain.

It is known that the enzyme glucose isomerase can transform D-glucose into D-fructose, which has found increasingly wider application in food processing industry and dietic foods in a number of developed countries. Glucose isomerase, in combination with a complex of amylolytic enzymes α-amylase and glucoamylase), enables the production of glucose-fructose syrups and of fructose directly from starch, using enzymes.

Some methods for obtaining of glucose isomerase have been known since 1957 when Marshall R. O. and Kooi E. R. demonstrated for the first time the possibility of direct conversion of D-glucose into D-fructose by means of cells belonging to the bacterial strain *Pseudomonas hydropuila N.* 491 and 492. For obtaining of glucose isomerase, microorganisms of the genus Streptomyces and above all the species *Str.phaeochromogenes, Str.venezuelae, Str.griseus, Str.wedmorensis, Str.albus, Str.flavovirens, Str.achromogenes, Str.achinatus, Str.olivocinereus, Str.achromogenes, Str.olivaceus* and others are most widely used. Besides the genus streptomyces there are other active producers such as proactinomyces and actinomyces belonging to other genera: e.g. Nocardia, Micromonospora, Actinoplanes, Thermoactinomyces, Thermopolyspora and also some bacterial strains belonging to the genera Aerobacter, Acetobacter, Lactobacillus, Bacillus, Arthrobacter and Flavobacterium.

The already known methods for obtaining of glucose isomerase have a number of disadvantages connected mainly with the fact that the strain producers rarely combine a high ratio of glucose isomerase activity with a favorable temperature and pH optimum of the enzyme. The temperature of the isomerization process, lower than 60°–65° C., leads to the danger of microbe pollution of the colony. The increase of the temperature to 90° C. decreases the stability of the enzyme, and results in coloration of the syrup and some changes in the viscosity. As far as industrial application is concerned the most favorable pH is from 6.5 to 7.0 because when the pH is over 7.0 an alkaline isomerization of glucose is carried out with the formation of D-psicose and coloration of the syrup, and a lower pH (below 5.5) causes an irreversible denaturation of the enzyme.

The object of this invention is to provide a method for obtaining of glucose isomerase from a streptomyces strain which has high activity with a high temperature optimum and a favorable pH of the enzyme.

The strain of Streptomyces sp.N.1339, used as a producer of glucose-isomerase, has been isolated from Bulgarian soil. 874 streptomyces strains have been screened for its discovery. The screening has been carried out on the modified synthetic culture medium N.1 developed by Krassilnikov, the selection being realized on two substrate levels with the use of xylose and xylane. Under these conditions 18 streptomyces strains have been discovered which can develop and produce the enzyme glucose isomerase. Of these streptomyces sp. N.1339 has proven to be the most effective for industrial purposes. The strain has been placed in the collection of the Bulgarian State Institute for Drug Control, bul. Vladimir Zaimov N.26 on Sept. 29, 1979 and is available under number 144 and has the following morphological and biochemical characteristics.

On culture medium 1 with a mineral source of nitrogen (using the technique of G. F. Gause and collaborators) the colonies are usually oval in shape, with unshaped edges, flat with a convex center-like dome and slightly folded. The sporangia are spiral with no more than 1–3 coils.

On some culture media are formed coremia. The growth is good. The spores are elongated with sharply cut ends and uneven surface. Their size is 0.4–0.9 microns in length and 0.3–0.6 microns in width. The ends have well defined corners. In some cases the spores are slightly concave in the middle. They are formed by means of fragmentation. The colonies are oval, with unshaped edges, flat, with a convex dome-shaped center, slightly folded, in some cases radially segmentated.

The color of the air and the substrate mycelium is determined according to the color scale of A. S. Bondartsev and the scale of Tresner—Backus.

With the different culture media the color of the air mycelium changes from light-grey to dark-grey ($a^4-a^2$) depending on the carbon and nitrogen sources. On culture medium 1 with a mineral source of nitrogen (after G. F. Gause and collaborators) the color is mousy-grey ($a^4$) to dark-grey ($a^2$) and on culture medium 2 with an organic source of nitrogen (after G. F. Gause) the color is dark-grey ($a^2$).

On culture media with different carbon and nitrogen sources the air mycelium is grey to dark-grey.

On culture medium 1 with a mineral source of nitrogen (after G. F. Gause and collaborators) the substrate mycelium has a light lemon color to yellow-orange ($d^5-d^2$). On culture medium 2 with an organic source of nitrogen (after G. F. Gause and collaborators) the substrate mycelium is golden-yellow and after a prolonged cultivation becomes almost chestnut ($m^7-O^7$).

On culture media with different carbon and nitrogen sources the substrate mycelium is from yellow to yellow-greyish-green.

On a culture medium of meat-pepton agar. Low growth. Air mycelium-white, very scarce. Substrate mycelium—colorless.

On a culture medium of potato-glucose agar. Growth very good. Air mycelium grey to dark-grey. Substrate mycelium light-brown to dark-brown, on the edge of the colony-yellow. Pigment in the center yellow.

On a culture medium of Tchapek with sucrose. Medium growth. Air mycelium light-grey. Substrate mycelium-beige.

On a Tchapek culture medium with glucose. Medium growth. Air mycelium greyish. Substrate mycelium cream-colored.

On a culture medium with sucrose. Good growth. Air mycelium grey. Substrate mycelium yellow.

On amylum agar culture medium. Medium growth. Air mycelium light-grey, with pale ashy color. Substrate mycelium yellow, lemon-color.

On amylium-ammonia culture medium after Mishustin. Good growth. Air mycelium grey to dark-grey. Substrate mycelium yellow, light-yellow.

On synthetic medium after Krassilnikov. Growth low to medium. Air mycelium beige grey. Substrate mycelium-yellow.

On CPI after N. A. Krassilnikov. Good growth. Air mycelium milk-grey, blue-grey. Substrate mycelium yellow-greyish-green.

On CPII after N. A. Krassilnikov. Good growth. Air mycelium grey, white exudate is separated. Substrate mycelium cream-grey.

On CPIII after Krassilnikov. Good growth. Air mycelium grey. Substrate mycelium yellow, lemon-colored.

On CPIV after N. A. Krassilnikov. Medium growth. Air mycelium light-grey, greyish. Substrate mycelium cream-colored.

On CPV after N. A. Krassilnikov. Low growth. Air mycelium-white. Substrate mycelium-beige, dark-cream-colored.

On synthetic medium after Vaxman. Medium growth. Air mycelium-white, on separate parts-grey. Substrate mycelium-yellow to orange.

On meat-amylum agar. Medium growth. Air mycelium-grey. Substrate mycelium-yellow.

On peptone agar. Good growth. Air mycelium-grey to dark-grey. Substrate mycelium-colorless with a shade of the air mycelium.

On glucose-asparagine agar. Medium growth. Air mycelium-light-grey. Substrate mycelium-yellow-cream-colored.

On glycerine-asparagine agar. Good growth. Air mycelium-light-grey, becoming grey in the process of ageing. Substrate mycelium-dark yellow.

On tyrosine agar. Medium growth. Air mycelium-grey, in some colonies to greyish-yellow. Substrate mycelium-dark-yellow to orange.

On tyrosine-caseine-nitrate agar. Medium growth. Air mycelium-ashy-grey. Substrate mycelium-yellow.

On glucose-tyrosine agar. Good growth. Air mycelium-cream-grey to grey. Substrate mycelium-yellow-brown.

On saccharose-nitrate agar. Medium growth. Air mycelium-grey. Substrate mycelium-cream-yellow.

On glycerol-calcium-malate agar. Good growth. Air mycelium-light-grey to grey. Substrate mycelium-yellow-orange.

On peptine-beef agar. Good growth. Air mycelium-grey. Substrate mycelium-colorless to beige.

On oats agar. Growth-very good. Air mycelium-grey. Substrate mycelium-light yellow.

On tomato agar. Good growth. Air mycelium-dark-grey. Substrate mycelium-terracotta-color.

On lead-acetate agar. Low growth. Air mycelium greyish. Substrate mycelium-yellow-brown.

On iron-peptone agar. Medium growth. Air mycelium-mousey-grey. Substrate mycelium-colorless with a grey shade from the air mycelium.

On yeast-malt agar. Growth good. Air mycelium-grey. Substrate mycelium-orange.

Strain tolerance towards NaCl. It shows low tolerance towards the concentration of sodium chloride in the medium. The maximum concentration is 4%. Under this concentration the strain tolerance is low. Air mycelium is white. The substrate mycelium is yellow. A concentration higher than 1% has a negative influence on the degree of sporulation.

It peptonizes fatless milk. In the beginning of the peptonization the reaction is acidic, and after a while turns to alkaline. It waters down gelatin. It grows very well on a sucrose medium, but doesn't invert sucrose. It grows very well on a amylum agar and hydrolyzes starch well.

It doesn't decompose cellulose and doesn't reduce nitrates to nitrites. It liberates hydrogen sulphide. It grows on potatoes. Hemolysis - positive. Tyrosinase - negative.

It has been found out that on basic culture medium of Pridham and Gottlieb the growth is good in the presence of the following carbon sources: glucose, fructose, levulose, xylose, maltose, cellobiose, galactose, mannitol, arabinose, dextrose, ribose and glycerol.

The strain absorbs salicin on a small scale.

It doesn't absorb carbon sources such as lactose, sorbite, inosite, sucrose and raffinose.

Some differences in the pigmentation of the air and substrate mycelium are found depending on the source of carbon. It has been found out that on modified basic culture medium of Pridham and Gottlieb the growth of the strain is good in the presence of the following sources of nitrogen: $NH_4Cl$, $(NH_4)_2SO_4$ $(NH_4)_2HPO_4$, $NH_4H_2PO_4$, $NH_4NO_3$, and carbamide and in the presence of $Na_2HPO_4$.

The growth is moderate on a culture medium with $NaNO_3$. The strain doesn't grow on a culture medium with $NaNO_2$.

A very good growth of the strain has been observed on culture media with the following amino-acids: asparaginic acid, asparagine, proline, cystine, tyrosine. The growth is moderate on a culture medium with valine, hydroxyproline, phenylalanine, leucine and alanine. The strain doesn't grow on a culture medium with glutamic acid.

Depending on the source of nitrogen some differences in the pigmentation of the air and the substrate mycelium have been discovered. Based upon some characteristics the streptomyces strain of the invention resembles *Streptomyces griseoflavus,* belonging to the series Gray after Bergey (1974)—*Actinomyces griseoflavus* of the Flavus group after N. A. Krassilnikov—1970. The latter is distinguished by a number of morphological—cultural and physiological—biochemical properties described in the species characterization by Bergey (1974) and N. A. Krassilnikov (1970). *Streptomyces griseoflavus,* for example, has elongated rod-like and oval spores with smooth surface; it shows tolerance towards NaCl from 7 to 10%. It hydrolyses starch weakly. It absorbs sucrose and sorbite and doesn't absorb galactose. Therefore streptomyces strain N 1339 is not identical with the similar *Streptomyces griseoflavus* (*Actinomyces griseoflavus*).

That is why it is referred to as Streptomyces sp. N 1339, belonging to the Gray series after Bergey (1974) and the Flavus group after N. A. Krassilnikov (1970).

The strain - producer is cultivated in Erlenmeyer flasks of 500 ml. containing 50 ml. fermentation culture medium for 36 to 96 hours under a temperature of 24° to 36° C., initial pH of cultivation from 6.5 to 9.0 on a shaker with 180–320 revolutions per minute.

Isomerization of glucose to fructose by means of glucose isomerase of the strain Streptomyces sp. N 1339 can be carried out through a direct treatment with fresh mycelium (separated through centrifugation at 12000 revolutions per minute and washed three times with 0.05 M phosphate buffer with pH 7.0) or with dried mycelium (air-dried or acetone-dried cells): with enzyme solution (obtained after a supersonic disintegration or autolysis of cell material and separation of supernatant through centrifugation at 15,000 rev/min.) with culture centrifugate, containing extracellular isomerase or cells made immobile on a hard carrier.

The fructose, formed in the reacting mixture is determined according to the cystein-carbazole method (19)

and the activity of the strain is expressed in mg. of fructose per ml. culture liquid or in International glucose-isomerase units (GIU). One GIU is equal to the quantity of enzyme which at 70° C. and pH 7.0, 1 M glucose solution in 0.05 M phosphate buffer, $1.10^{-4}$ M $CaCl_2$. $6H_2O$ and $1.10^{-2}$ M $MgSO_4$. $7H_2O$ tranforms in one minute $1\mu$ of glucose into $1\mu$ of fructose.

The advantages of the method according to the invention are the following:

For obtaining of glucose-isomerase the strain streptomyces sp. N.1339 was used. This strain possesses high biosynthetic capabilities for the enzyme (12000-20000 GIU) which exceeds by 4 to 20 times the activity of strain producers, known in the patent literature. The enzyme which is obtained is marked by a high temperature optimum (70°) under low optimum concentrations of $CO^{++}$ ($1.10^{-4}$ M) and ($1.10^{-2}$ M) in the isomerization mixture. It has a favorable pH-optimum (7.0) and considerable thermostability between 40° and 65° C.

The invention is illustrated by the following examples:

EXAMPLE 1

The strain producer is maintained in test tubes with slant agar on culture media with the following composition:

1. Xylose culture medium
    xylose—20 g
    agar—20 g
    $KNO_3$—1.0 g
    $K_2HPO_4$—0.5 g
    $MgSO_4.7H_2O$—0.5 g
    NaCl—0.5 g
    $CaCO_3$—1.0 g
    $FeSO_4$—0.001 g
    water up to 1 l.
2. Potato - glucose agar:
    Potato extract from 300 g. boiled potatoes
    glucose 10 g
    agar 20 g
    water up to 2 l.

It is recommended that for maintenance of the strain both culture media should be alternated.

To a well germinated material from 10-15 days culture on culture medium 1 or 2 (1 is recommended) 6 ml inoculation culture medium is added, having the following composition:
    xylose—1.0%
    tryptone—2.0%
    $MgSO_4 7H_2O$—0.1%
    $K_2HPO_4$—0.25%

A wash-out of the cell mass is carried out and the test-tube is put on a shaker for 24 hours under 30° C. and at 240 revolutions per minute. From thus adapted culture, an inoculation medium with the following composition is sown.
    xylose—1.0%
    maize extract—3.0% (in dry weight)
    $MgSO_4$. $7H_2O$—0.1%
    $K_2HPO_4$—0.25%
    agar—0.1%

After 60 hours of cultivation under the above mentioned conditions 5% of the inoculum is introduced into a fermentation culture medium with the following composition:
    xylose—1%
    maize extract—3.0% (in dry weight)
    $MgSO_4$. $7H_2O$—0.1%
    KCl—0.0075%
    $CoCl_2$. $6H_2O$—0.024%

The cultivation is carried out in Erlenmeyer flasks of 500 ml. containing 50 ml fermentation culture medium. It is carried out for 60 hours under 30° C. on a shaker at 240 revolutions per minute. The initial pH of cultivation is 8.5.

After 60 hours of cultivation of Streptomyces sp.N.1339 there is obtained 140-220 g of a moist biomass per 1 l. of culture liquid.

EXAMPLE 2

Isomerization of glucose to fructose by means of glucose-isomerase of the strain Streptomyces sp. N1339 is carried out under a temperature of 70° C., pH 7.0 in the presence of $CoCl_2 6H_2O$ in concentration $1 \times 10^{-4}$ M, $MgSO_4$. $7H_2O$ in concentration $1 \times 10^{-2}$ M and substrate concentration 1 M.

The activity of the strain Streptomyces sp. N 1339 is 130-215 mg fructose per 1 ml cultural liquid or 12 000-20 000 GIU per 1 l cultural liquid.

What we claim is:

1. A method for producing glucose isomerase comprising the steps of cultivating the enzyme producing strain Streptomyces sp. 1339 registration N.144 Bulgarian State Institute for Drug Control, for 36 to 72 hours in a culture medium with xylose as an indicator, the temperature being kept at 24° to 36° C., the initial pH of cultivation being from 6.5 to 9.0 and effective isomerization at a temperature of 50° to 80° C., and a pH of 6.0 to 9.0 in the presence of $1 \times 10^{-4}$ M $CoCl_2$. $6H_2O$ $1 \times 10^{-2}$ M $MgSO_4$. $7H_2O$ in 0.1 to 3 M of the substrate.

2. The method defined claim 1 wherein the culture medium which is used has the following composition:
    xylose—1.0 to 2.0%
    maize extract 1.5 to 4.0% (in dry weight)
    $MgSO_4$. $7H_2O$—0.05% to 0.2%
    KCl—0.005% to 0.01%
    $CoCl_2$. $6H_2O$—0.008% to 0.036%.

* * * * *